US00PP35328P2

(12) United States Plant Patent
Good

(10) Patent No.: US PP35,328 P2
(45) Date of Patent: Aug. 22, 2023

(54) ***WEIGELA* PLANT NAMED 'FLORACLAR'**

(50) Latin Name: *Weigela florida*
Varietal Denomination: FLORACLAR

(71) Applicant: Spring Meadow Nursery Inc., Grand Haven, MI (US)

(72) Inventor: Jeffrey W. Good, South Lyon, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/087,334

(22) Filed: Dec. 22, 2022

(51) Int. Cl.
*A01H 6/00* (2018.01)
*A01H 5/00* (2018.01)

(52) U.S. Cl.
USPC ..... Plt./226

(58) Field of Classification Search
USPC ..... Plt./226
See application file for complete search history.

*Primary Examiner* — Karen M Redden
(74) *Attorney, Agent, or Firm* — Cassandra Bright

(57) ABSTRACT

A new and distinct cultivar of *Weigela* plant named 'FLORACLAR' is disclosed, characterized by dark green to wine-colored leaves with yellow-gold marginal variegation. Plants are compact and round in habit, and lightly flowering with hot pink single salverform flowers. The new variety is a *Weigela*, normally produced as an outdoor garden plant.

2 Drawing Sheets

Latin name of the genus and species: *Weigela florida*.
Variety denomination: 'FLORACLAR'.

BACKGROUND OF THE INVENTION

The new *Weigela* cultivar is the product of a naturally occurring branch mutation of the variety *Weigela florida* 'Bramwell', U.S. Plant Pat. No. 18,513. The new variety was discovered by the inventor in August 2016 in South Lyon, Mich.

Asexual reproduction of the new cultivar 'FLORACLAR' by softwood cuttings was first performed in August 2017, at a commercial nursery in Grand Haven, Mich. Subsequent propagation has shown that the unique features of this cultivar are stable and reproduced true to type in multiple successive generations.

Date of first sale Jun. 21, 2022, in Grand Haven, Mich. This sale was made directly by the inventor or one who obtained the claimed invention directly or indirectly from the inventor. This sale and all public disclosures made between Jun. 21, 2022 and the filing of this application fall within the exception allowed under 102(b)(1).

SUMMARY OF THE INVENTION

The cultivar 'FLORACLAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FLORACLAR' These characteristics in combination distinguish 'FLORACLAR' as a new and distinct *Weigela* cultivar:

1. Dark green to wine-colored leaves with yellow-gold marginal variegation.
2. Compact, rounded habit.
3. Lightly flowering with hot pink single salverform flowers.
4. Stable characteristic to variegation.

PARENT COMPARISON

Plants of the new cultivar 'FLORACLAR' are similar to plants of the seed parent in most horticultural characteristics, however, plants of the new cultivar 'FLORACLAR' differ in the following:

1. Foliage of the new variety has yellow-gold marginal variegation, while foliage of the seed parent has no variegation.
2. The new variety is slightly floriferous, while the seed parent is quite floriferous.
3. Plants of the new variety are more compact than plants of the seed parent.

COMMERCIAL COMPARISON

Plants of the new cultivar 'FLORACLAR' can be compared to the commercial variety *Weigela florida* 'Kolmagira', U.S. Plant Pat. No. 20,384. These varieties are similar in most horticultural characteristics, however 'FLORACLAR' differs in the following:

1. Foliage of the new variety is dark green to wine-colored with yellow-gold marginal variegation. Foliage of this comparator is dark green colored with lighter yellowish-green marginal variegation which blushes pink.
2. The new variety is slightly floriferous, while this comparator is quite floriferous.
3. Flowers of the new variety are bright pink, while flowers of this comparator are bright and lighter pink.
4. Leaves of the new variety are narrower than leaves of this comparator.

BRIEF DESCRIPTION OF THE PHOTOGRAPHS

Figure 1:
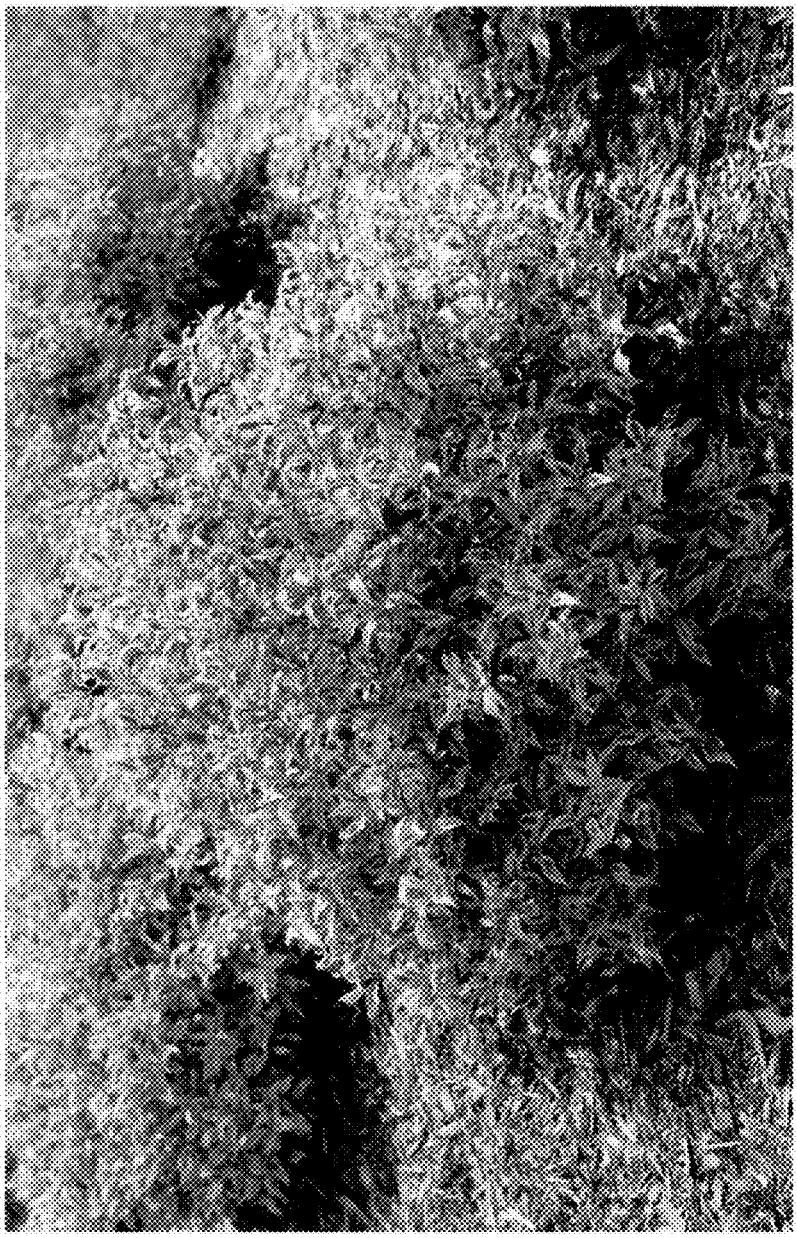

The accompanying photograph in FIG. 1 illustrates in full color typical plants of the new variety grown in a ground bed at about 2 years of age.

Figure 2:
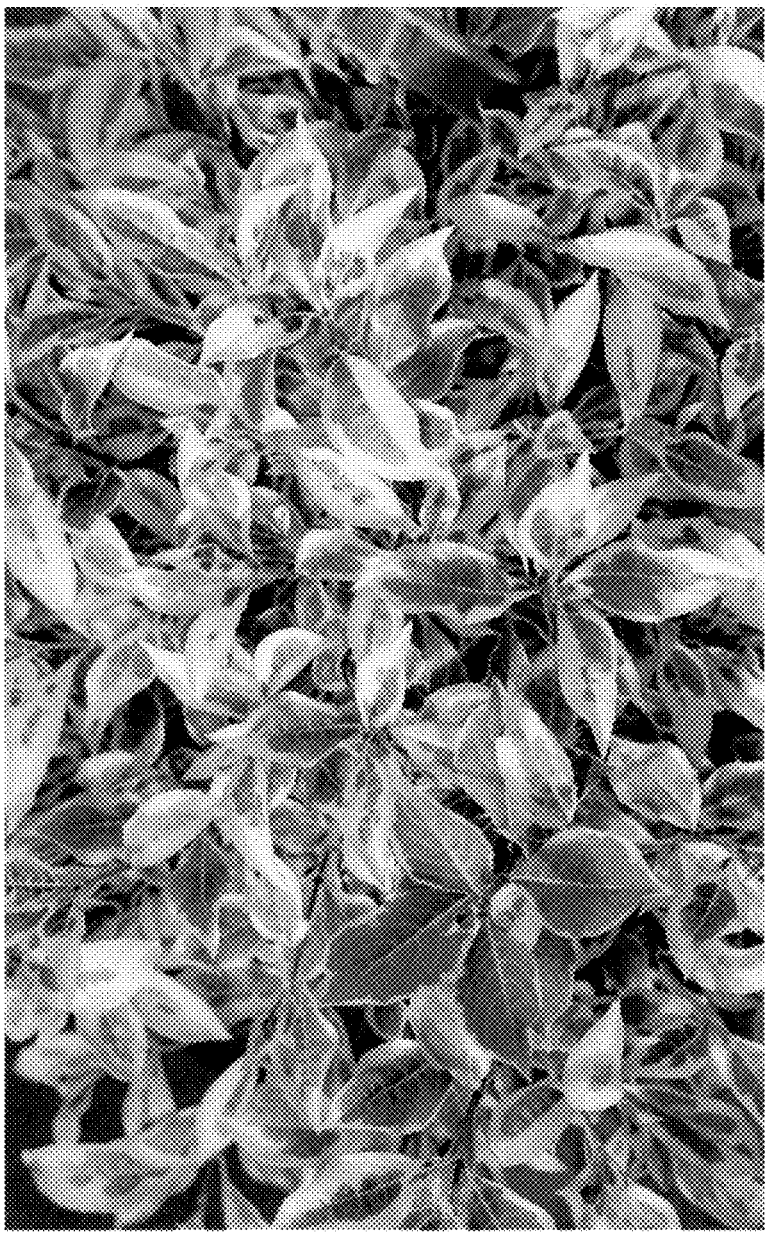

FIG. 2 is a close-up view of typical foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'FLORACLAR' plants grown in a polyhouse in Grand Haven, Mich. Measurements were taken during May of 2022. The plants were 2 to 3 years old. The growing temperature ranged from approximately 18° C. to 27° C. during the day and 5° C. to 10° C. at night. Measurements and numerical values represent averages of typical plant types.

Botanical classification: *Weigela florida* 'FLORACLAR'.

PROPAGATION

Time to initiate roots: 15 days at 18° C. to 27° C.

Root description: Dense and freely branching. Thin and fibrous. White in color, not effectively measured with a color chart.

Time to produce a rooted young plant: Approximately 60 days.

PLANT

Plant type: Perennial shrub.

Age of plant described: Approximately 2 to 3 years old.

Growth habit: Upwards and outwards.

Pot size of plant described: 3-gallon container.

Overall plant shape: Upright and mounded.

Height: Around 40 cm in a trimmed 3-gallon container.

Plant spread: Around 60 cm in a trimmed 3-gallon container.

Plant vigor: Quite vigorous.

Growth rate: Fast.

Branching characteristics: Basal branching, pinching required.

Length of primary lateral branches: 35 cm.

Diameter of lateral branches: 5 mm.

Quantity of lateral branches: About 10.

Stem:

- *Appearance*.—Rounded, two small ridges 180° apart on stem.
- *Stem strength*.—Strong.
- *Aspect*.—30° to 70°.
- *Color*.—RHS Yellow-Green 145B with tinges of Greyed-Orange 176B developing near terminal end.
- *Pubescence*.—Some, along two small ridges set 180° apart on stem.

Internode length: 5 to 6 cm.

FOLIAGE

Leaf:

- *Arrangement*.—Opposite.
- *Leaf shape*.—Narrowly elliptic to oblanceolate.
- *Length*.—3 to 4 cm.
- *Width*.—1 to 2 cm.
- *Apex*.—Acuminate.
- *Base*.—Attenuate.
- *Margin*.—Serrulate.
- *Texture of top surface*.—Coriaceous.
- *Texture of bottom surface*.—Coriaceous, veins have a raised texture.
- *Pubescence*.—None.
- *Color*.—Young foliage upper side: RHS Yellow-Green 147B with 145A variegation along margins. Young foliage under side: RHS Yellow-Green 147B with 145A variegation along margins. Mature foliage upper side: Yellow-Green 147B becoming tinted with Brown 200A and with Yellow-Green 145A variegation along margins. Mature foliage under side: Yellow-Green 147B becoming tinted with Brown 200A and with Yellow-Green 145A variegation along margins.
- *Venation*.—Pattern: Pinnate. Color upper side: RHS Yellow-Green 145A. Color under side: RHS Yellow-Green 145A.
- *Petiole*.—Length: 5 mm. Diameter: 2 mm. Petiole color upper side: RHS Yellow-Green 145A. Petiole color lower side: RHS Yellow-Green 145A. Petiole Texture: Slightly pubescent.

FLOWER

Natural flowering season: Late spring to early summer.

Arrangement: Single or small groups (2-3) of salverform flowers emerging from leaf apices at lateral branch termini.

Individual flowers:

- *Flower shape*.—Salverform.
- *Flower aspect*.—Upwards and outwards.
- *Flowering arrangement*.—Salverform flowers arranged in groups of 1 to 3.
- *Size*.—Diameter: 2 cm. Depth: 2.25 cm. Throat diameter proximal: 5 mm. Throat diameter distal: 2 cm. Tube length: 2 cm.
- *Persistence*.—Self-cleaning.
- *Fragrance*.—None.

Bud:

- *Shape*.—Obovate to spatulate.
- *Length*.—1 to 1.5 cm.
- *Diameter*.—3 to 5 mm.
- *Color*.—RHS Red-Purple 60C.

Petal:

- *Petal arrangement*.—Cruciform.
- *Number of petals per flower*.—4.
- *Petal shape*.—Rounded-orbicular.
- *Petal base*.—Fused at throat.
- *Margin*.—Entire to slightly sinnuate.
- *Tip shape*.—Obtuse.
- *Length*.—1 cm.
- *Width*.—1 cm.
- *Texture*.—Upper: Soft, smooth, delicate. Lower: Soft, smooth, delicate.
- *Throat texture*.—Soft, glabrous.
- *Tube texture*.—Soft, glabrous.
- *Color*.—When opening: Upper side: RHS Red-Purple 63B. Under side: RHS Red-Purple 63A. Fully open: Upper side: RHS Red-Purple 63B. Under side: RHS Red-Purple 63A.
- *Flower tube*.—Color: RHS Red-Purple 63A.
- *Throat*.—Color: RHS Red-Purple 63A.

Sepal:

- *Arrangement*.—Whorl.
- *Appearance*.—Unguiculate.
- *Number*.—4.
- *Shape*.—Narrowly triangular.
- *Tip*.—Acuminate.
- *Base*.—Fused.
- *Margin*.—Entire.
- *Length*.—1 cm.
- *Width*.—1 mm.
- *Texture, upper*.—Glabrous.
- *Texture, lower*.—Glabrous.

*Color*.—Upper surface at maturity: RHS Yellow-Green 146D with tints/streaking of Red-Purple 63A. Under surface at maturity: RHS Yellow-Green 146D with tints/streaking of Red-Purple 63A.

*Calyx shape*.—Crown-like.

Peduncle:

*Length*.—1 cm.

*Diameter*.—2 mm.

*Color*.—RHS Brown 200A with Yellow-Green 145A on the underside.

*Angle*.—45°.

*Strength*.—Good.

*Texture*.—Glabrous.

Pedicel: None.

REPRODUCTIVE ORGANS

Stamens:

*Number*.—4.

*Filament length*.—2 cm.

*Filament color*.—RHS Red-Purple 63A.

Anthers:

*Shape*.—Linear.

*Length*.—3 mm.

*Color*.—RHS Yellow-White 158B.

*Pollen color*.—RHS Yellow-White 158B.

*Pollen amount*.—Some.

Pistil:

*Number*.—1.

*Length*.—2.5 cm.

*Style*.—Length: 2.25 cm. Color: RHS Red-Purple 63A.

Stigma:

*Color*.—RHS Yellow-green 145D.

*Shape*.—Globular.

OTHER CHARACTERISTICS

Seeds and fruits: Not observed to set fruit and seeds.

Disease/pest resistance: Neither resistance nor susceptibility to normal diseases and pests of *Weigela* have been observed Temperature tolerance: The new variety tolerates temperatures between −31° C. to 38° C.

What is claimed is:

1. A new and distinct cultivar of *Weigela florida* plant named 'FLORACLAR' as herein illustrated and described.

* * * * *